United States Patent
Uellner

(10) Patent No.: US 9,326,585 B2
(45) Date of Patent: May 3, 2016

(54) HAIR COLORING PROCESS

(71) Applicant: KAO GERMANY GMBH, Darmstadt (DE)

(72) Inventor: Martin Uellner, Darmstadt (DE)

(73) Assignee: KAO GERMANY GMBH, Darmstadt (DE)

( * ) Notice: Subject to any disclaimer, the term of this patent is extended or adjusted under 35 U.S.C. 154(b) by 0 days.

(21) Appl. No.: 14/413,620

(22) PCT Filed: Jul. 18, 2013

(86) PCT No.: PCT/EP2013/065162
§ 371 (c)(1),
(2) Date: Jan. 8, 2015

(87) PCT Pub. No.: WO2014/016193
PCT Pub. Date: Jan. 30, 2014

(65) Prior Publication Data
US 2015/0136168 A1    May 21, 2015

(30) Foreign Application Priority Data

Jul. 27, 2012  (EP) .................................. 12178210

(51) Int. Cl.
| | | |
|---|---|---|
| *A61Q 5/10* | (2006.01) | |
| *A45D 44/00* | (2006.01) | |
| *A61K 8/46* | (2006.01) | |
| *A61K 8/49* | (2006.01) | |
| *A61Q 5/06* | (2006.01) | |

(52) U.S. Cl.
CPC .............. *A45D 44/005* (2013.01); *A61K 8/466* (2013.01); *A61K 8/498* (2013.01); *A61Q 5/065* (2013.01); *A61K 2800/4322* (2013.01); *A61K 2800/882* (2013.01)

(58) Field of Classification Search
CPC ....... A61Q 5/065; A61K 8/416; A61K 8/342; A61K 8/36; A61K 2800/21; A61K 2800/432
USPC ..................................... 8/405; 132/202, 208
See application file for complete search history.

(56) References Cited

U.S. PATENT DOCUMENTS

2009/0038086 A1*  2/2009  Molenda ................ A61K 8/891
                                                                    8/407

FOREIGN PATENT DOCUMENTS

| | | |
|---|---|---|
| JP | 2004-061439 A | 2/2004 |
| JP | 2007-212140 A | 8/2007 |
| WO | 01/87245 A2 | 11/2001 |

OTHER PUBLICATIONS

International Search Report dated Oct. 7, 2013 and mailed Oct. 16, 2013.

* cited by examiner

*Primary Examiner* — Eisa Elhilo
(74) *Attorney, Agent, or Firm* — Norris McLaughlin & Marcus LLP

(57) ABSTRACT

Present invention relates to a hair coloring process which allows visualization of the color to be achieved prior to coloring hair using a sheet (1) comprising two or more areas (2) having each different natural hair color.

13 Claims, 1 Drawing Sheet

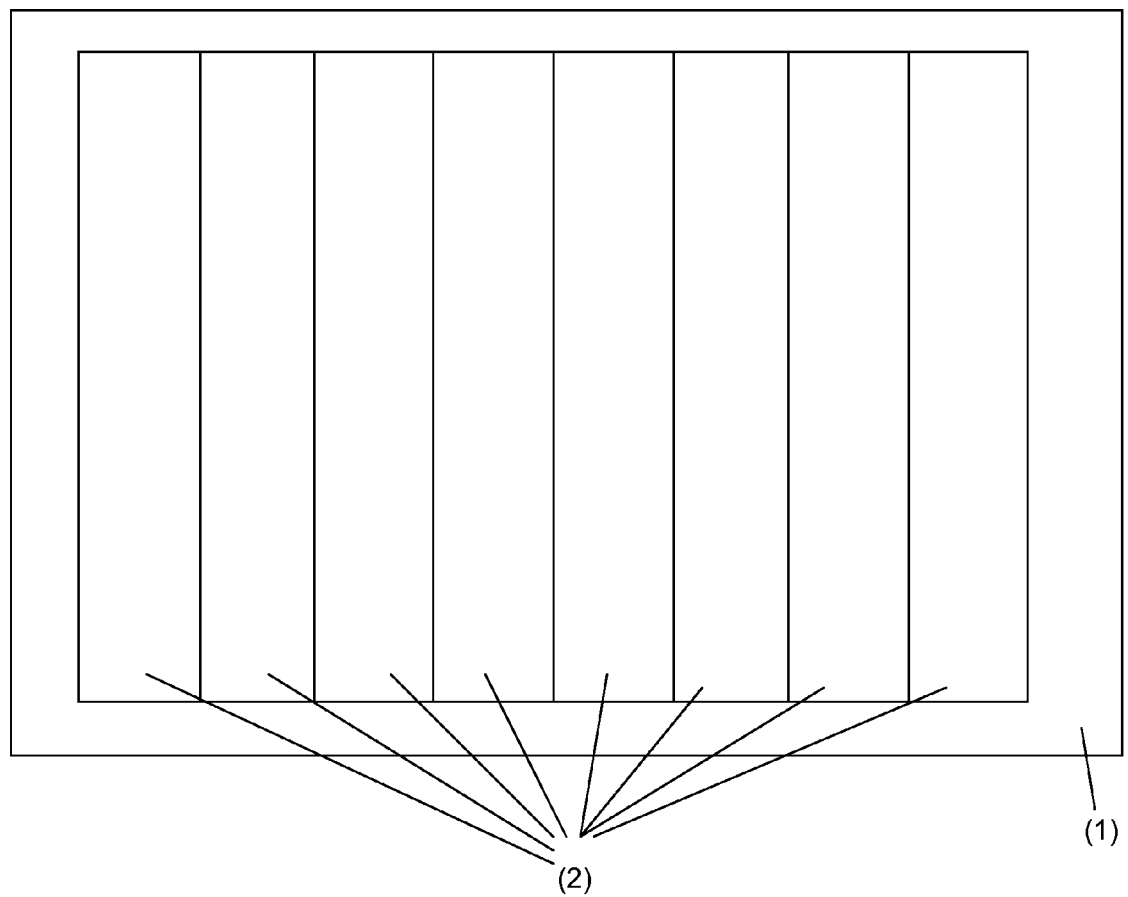

HAIR COLORING PROCESS

This application is a 371 application of PCT/EP2013/065162 filed Jul. 18, 2013, which claims foreign priority benefit under 35 U.S.C. §119 of European Application No. 12178210.6 filed Jul. 27, 2012, the disclosures of which are all incorporated herein by reference.

Present invention relates to a hair coloring process which allows visualization of the color to be achieved prior to application of coloring composition onto hair using a sheet comprising two or more parts having each different natural hair color.

Hair coloring is used in a daily hair dressing practice for beautifying hair. Coloring hair with oxidative dyes involves partly or completely degradation of existing hair natural and/or artificial color with the aid of oxidizing agents especially hydrogen peroxide and simultaneously changing hair color with polymerization of the oxidative dye precursors and/or couplers. In such a process it is relatively easy to provide a view to the customer the final color with the use of standard streaks provided by almost all hair color provider.

On the other hand, when coloring with the aid of direct dyes and especially in the absence of any oxidizing agent, prediction of the final hair color is almost impossible since the existing hair color is not removed and/or degraded at all. The problem is especially aggravated when more than one ready to use composition must be mixed prior to application to reach the final color. In such a case, there may not be any standard colored streak provided by the supplier and therefore, color reviewing is impossible if the final intended color meets the expectations of the customers. This brings about problems because in the case of dissatisfaction, additionally chemically aggressive compositions have to be used to remove the added color and hair coloring must be carried out again. Therefore, a hair coloring service can easily end up time and cost intensive experience, on one hand, to hair dresser providing the service and, on the other hand, customer.

Therefore, there is a great need for a simple solution in a way of visualizing the resulting hair color prior to carrying out the real process.

The inventors of the present invention have surprisingly found out that a sheet comprising two or more parts colored with the color of various natural hair may easily be used to visualize the color finally be achieved on the head of customer by applying the coloring composition solely comprising hair direct dyes onto the said sheet. By doing so, hair dresser providing the coloring service and customer willing to change hair color can easily review approximately the final color to be achieved at the end of the service.

Therefore, the first object of the present invention is a hair coloring process with an aqueous composition comprising solely one or more direct dye(s) wherein prior to application onto hair it is first applied onto a sheet (1) comprising two or more areas (2) having each different natural hair color to visualize the color of hair at the end of the coloring process and applied the said composition onto hair and after processing 1 to 45 min rinsed off from hair, hair is optionally shampooed and optionally dried.

In the preferred embodiment of the present invention, aqueous hair coloring composition used in the process of the invention is resulting from mixing two or more ready to use hair coloring compositions comprising solely one or more hair direct dyes.

The sheet (1) comprising two or more areas (2) having each different natural hair color comprises preferably 2 to 15 areas having each different natural hair color, more preferably 3 to 10, most preferably 4 to 8 and in particular 4 to 6 areas having each different hair color.

In a further preferred embodiment of the present invention the areas having different natural hair color are parallel to each other as on FIG. 1.

FIG. 1: Sheet with areas having each different natural hair color

In a further preferred embodiment of the present invention is that the sheet is made of cellulosic wood free paper weighing 140 g/m$^2$.

Further object of the present invention is the use of a sheet (1) made of cellulosic wood free paper weighing 140 g/m$^2$ and comprising two or more areas (2) having each different natural hair color in a hair coloring process wherein hair coloring compositions comprising solely hair direct dyes.

In particular, further object of the present invention is the use of a sheet made of cellulosic wood free paper weighing 140 g/m$^2$ and comprising two or more areas having each different natural hair color in a hair coloring process wherein hair coloring compositions comprising solely hair direct dyes for visualizing to be achieved hair color prior to actual hair coloring is carried out.

Hair coloring composition used in the process of the present invention has a pH in the range of 1 to 10, preferably 1.5 to 9.5, more preferably 2 to 9, most preferably 2.2 to 8.5. pH of the compositions are adjusted with the well known organic and/or inorganic acids and basis. Preferably, aqueous coloring composition comprises at least one carboxylic acid. Suitable ones are lactic acid, citric acid, malic acid, maleic acid. Most preferred is lactic acid.

Aqueous coloring compositions may be in any form known in the art. Preferred are solutions, gels, foams, thickened liquids and emulsions. Most preferred are gels and emulsions.

Accordingly, aqueous compositions in the form of gels comprise at least one gelling agent at a concentration in the range of 0.1-5%, preferably 0.1-3% and most preferably 0.1-2% by weight calculated to the total composition. Suitable ones may be of the know polymers forming gel. Preferred are acrylates and derivatives, cellulose and its derivatives such as hydroxyalkyl celluloses, e.g. hydroxyethyl cellulose, hydroxypropyl cellulose, hydroxypropyl methyl cellulose, bio polymers such as bio-polyheterosaccharides such as xanthan gum, guar gum and the alkoxylation products thereof. The most preferred gelling agent is xanthan gum.

In case aqueous composition is an emulsion then it comprises at least one fatty alcohol and at least one emulsifying agent.

Aqueous colouring composition comprises at least one fatty alcohol or mixture of fatty alcohols having alkyl chain length of 14 to 22 C atoms which may be straight or branched, saturated or unsaturated. Examples to suitable fatty alcohols, without limiting, are myristyl alcohol, cetyl alcohol, stearyl alcohol, behenyl alcohol, oleyl alcohol and cetostearyl alcohol, octyldodecanol. The most preferred is cetostearyl alcohol well known with its trade name Lanette O or as Lanette N in mixture with sodium cetearyl sulfate from Cognis. Total fatty alcohol concentration is in the range of 1 to 20% by weight, calculated to total composition.

Aqueous coloring composition comprises emulsifying agents selected from anionic, non-ionic, amphoteric (or zwiterionic) and/or cationic surfactants. The most preferred are anionic, non-ionic and cationic surfactants.

The preferred non-ionic emulsifiers are ethoxylated fatty alcohols with an alkyl chain of 12 to 24 C atoms and with number of ethoxyl groups of 2 to 50, preferably 10 to 30. Examples are ceteth-20, seteareth-30, palmeth-20, steareth- 20, beheneth-20 etc. These compounds are named according to the fatty alcohol they are originating and number of ethoxyl groups is given at the end. These compounds are well known emulsifiers and found in any cosmetic ingredient book.

Further suited nonionic surfactants are, especially in mixture with fatty alcohol ethoxylates, for example, long-chain fatty acid mono- and dialkanolamides, such as coco fatty acid mono- or diethanolamide and myristic fatty acid mono or diethanolamide, stearic acid mono or diethanolamide.

Further nonionic surfactants suited again especially in admixture with fatty alcohol ethoxylates mentioned above are alkyl polyglucosides of the general formula $$R_1-O-(R_2O)_n-Z_x,$$

wherein $R_1$ is an alkyl group with 8 to 18 carbon atoms, $R_2$ is an ethylene or propylene group, Z is a saccharide group with 5 to 6 carbon atoms, n is a number from 0 to 10 and x is a number between 1 and 5.

Further additionally useful nonionic surfactants are, for example, the various sorbitan esters, such as polyethylene glycol sorbitan stearic acid ester, fatty acid polyglycol esters or poly-condensates of ethyleneoxide and propyleneoxide, as they are on the market, for example, under the trade name "Pluronics®", as well as fatty alcohol ethoxylates.

Anionic surfactants suitable are of the sulfate, sulfonate, carboxylate and alkyl phosphate types, for example, the known $C_{10}$-$C_{18}$-alkyl sulfates, and in particular the respective ether sulfates, for example, $C_{12}$-$C_{14}$-alkyl ether sulfate, lauryl ether sulfate, especially with 1 to 4 ethylene oxide groups in the molecule, monoglyceride (ether) sulfates, fatty acid amide sulfates obtained by ethoxylation and subsequent sulfatation of fatty acid alkanolamides, and the alkali salts thereof, as well as the salts of long-chain mono- and dialkyl phosphates.

Additional anionic surfactants useful within the scope of the invention are α-olefin sulfonates or the salts thereof, and in particular alkali salts of sulfosuccinic acid semiesters, for example, the disodium salt of monooctyl sulfosuccinate and alkali salts of long-chain monoalkyl ethoxysulfosuccinates.

Suitable surfactants of the carboxylate type are alkyl polyether carboxylic acids and the salts thereof of the formula $$R_3-(C_2H_4O)_n-O-CH_2COOX,$$

wherein $R_3$ is a $C_8$-$C_{20}$-alkyl group, preferably a $C_{12}$-$C_{14}$-alkyl group, n is a number from 1 to 20, preferably 2 to 17, and X is H or preferably a cation of the group sodium, potassium, magnesium and ammonium, which can optionally be hydroxyalkyl-substituted, as well as alkyl amido polyether carboxylic acids of the general formula

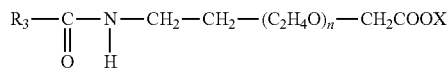

wherein $R_3$ and X have the above meanings, and n is in particular a number from 1 to 10, preferably 2.5 to 5.

Such products have been known for some time and are on the market, for example, under the trade name "AKYPO®" and "AKYPO-SOFT®".

Also useful are $C_8$-$C_{20}$-acyl isethionates, alone or in admixture with other anionic surfactants, as well as sulfofatty acids and the esters thereof.

Further suitable anionic surfactants are also $C_8$-$C_{22}$-acyl aminocarboxylic acids or the water-soluble salts thereof. Especially preferred is N-lauroyl glutamate, in particular as sodium salt, as well as, for example, N-lauroyl sarcosinate, N—$C_{12}$-$C_{18}$-acyl asparaginic acid, N-myristoyl sarcosinate, N-oleoyl sarcosinate, N-lauroyl methylalanine, N-lauroyl lysine and N-lauroyl aminopropyl glycine, preferably in form of the water-soluble alkali or ammonium, in particular the sodium salts thereof, preferably in admixture with the above-named anionic surfactants.

Suitable cationic surfactants are according to the formula,

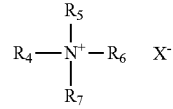

where $R_4$ is a saturated or unsaturated, branched or non-branched alkyl chain with 8-22 C atoms or $$R_5CONH(CH_2)_n$$

where $R_5$ is saturated or unsaturated, branched or non-branched alkyl chain with 7-21 C atoms and n has typical value of 1-4 or $$R_9COO(CH_2)_n$$

where $R_9$ is saturated or unsaturated, branched or non-branched alkyl chain with 7-21 C atoms and n has typical value of 1-4, and $R_5$, $R_6$ and $R_7$ are substituted or unsubstituted, straight or branched, saturated or unsaturated lower alkyl chain with 1 to 4 C atoms, and X is typically chloride, bromide, methosulfate.

Typical examples of those ingredients are cetyl trimethly ammonium chloride, stear trimonium chloride, stearamidopropyl trimonuim chloride, behentrimonium chloride, behenamidopropyl trimethylammonium chloride, stearoyl-ethyltrimonium chloride.

As further surfactant component, the colouring compositions according to the invention can also contain amphoteric or zwitterionic surfactants. Useful as such are in particular the various known betaines such as alkyl betaines, fatty acid amidoalkyl betaines and sulfobetaines, for example, lauryl hydroxysulfobetaine; long-chain alkyl amino acids, such as cocoaminoacetate, cocoaminopropionate and sodium cocoamphopropionate and -acetate have also proven suitable.

Total surfactant concentration is in the range of 0.5 to 15%, preferably 1 to 10%, more preferably 1 to 7.5% by weight calculated to total composition.

Composition of the present invention may further comprise one or more direct dyes. Suitable ones are cationic, anionic and neutral nitro dyes and their mixtures.

Suitable non-limiting examples to cationic ones are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green, Basic Orange 31, 1, Basic Red 2, Basic Red 12 Basic Red 22, Basic Red 76 Basic Red 51, Basic Violet 1, Basic Violet 2, Basic Violet 3, Basic Violet 10, Basic Violet 14, Basic Yellow 57 and Basic Yellow 87, and their mixtures.

Suitable non-limiting examples to anionic ones are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. And their mixtures.

Suitable non-limiting examples to nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-Amino-6-chloro-4-nitrophenol, picramic acid, 1,2-Diamino-4-nitrobenzol, 1,4-Diamino-2-nitrobenzol, 3-Nitro-4-aminophenol, 1-Hydroxy-2-amino-3-nitrobenzol and 2-hydroxyethylpicramic acid, and their mixtures.

Total concentration of one or more direct dyes is in the range of 0.001 to 15%, preferably 0.01 to 10%, more preferably 0.1 to 7.5% and most preferably 0.1 to 5% by weight calculated to total composition.

Aqueous coloring composition can comprise additionally fatty acids with 0 to 3 ethylenic bonds and with fatty acyl chain length of 12 to 22 C atom. Concentration of the fatty acids can be in the range of 0.1 to 10%, preferably 0.1 to 7.5% and most preferably 0.2 to 5% by weight calculated to the total composition. Non-limiting examples are myristic acid, palmitic acid, behenic acid, steraic acid, oleic acid, linoleic acid. The most preferred fatty acid is oleic acid.

Aqueous colouring composition can also contain cationic polymers as conditioning agents. Those are cationic cellulose type polymers know as Polymer JR type from Amerchol such as Polyquaternium 10 or cationic guar gum known with trade name Jaguar from Rhône-Poulenc and chemically for example Guar hydroxypropyl trimonium chloride. Furthermore, chitosan and chitin can also be included in the compositions as cationic natural polymers.

Furthermore, it has been found suitable those cationic polymers known with their CTFA category name Polyquaternium. Typical examples of those Polyquaternium 6, Polyquaternium 7, Polyquaternium 10, Polyquaternium 11, Polyquaternium 16, Polyquaternium 22 and Polyquaternium 28, Polyquaternium 30, Polyquaternium 37, Polyquaternium 36, Polyquaternium 46. Among those the most preferred one is the Polyquaternium 11 as well known with its trade name Gafquat from ISP and as Luviquat PQ from BASF.

Typical concentration range for any of the cationic conditioners mentioned above can be 0.01-5% by weight, preferably 0.03-2.5% by weight and more preferably 0.05-1.5% by weight.

Hair dyeing composition of the present invention preferably comprise an organopolysiloxane wherein at least one silicium atom is linked to an alkylene group having a heteroatom, in particular a nitrogen atom, with a poly-(N-acyl alkyleneimine) units of the formula

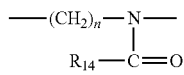

wherein n is a number from 1 to 5 and $R_{14}$ is hydrogen, a $C_1$-$C_{12}$-alkyl or cycloalkyl, aralkyl or aryl group.

Preferred organopolysiloxane polymers are those of the type disclosed in EP-A 640 643, in particular optionally quaternized aminoalkyl, in particular aminopropyl dimethyl polysiloxane/polyethyl oxazoline copolymers of the formula

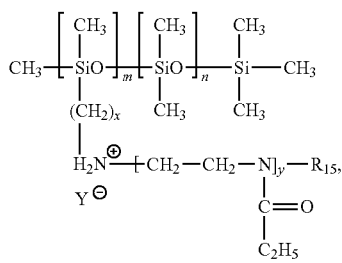

wherein m and n each are numbers from 20 to 10,000, in particular 50 to 7,000, especially 100 to 5,000, x is a number between 1 and 5, preferably 3, and y is a number from 5 to 30, $R_{15}$ is a $C_1$-$C_{12}$-alkyl or aryl group, in particular a methyl, ethyl or benzyl group, and $Y^-$ is an anion.

Especially suited are the organopolysiloxanes disclosed under the terms A-1, A-2 and A-3 on pages 12 to 13 of EP-A 640 643. The proportion of graft copolymers in the hair colouring compositions according to the invention ranges from 0.05% to 5%, preferably 0.1% to 2.5%, in particular 0.5% to 1.5% by weight, calculated to the total composition.

Aqueous coloring composition comprises preferably one or more organic solvents. Examples of such organic solvents are benzyloxy ethanol, benzyl alcohol, phenoxy ethanol, phenoxy isopropanol, methyl phenoxy ethanol, benzyl glycerol, N-benzyl formide, N-methyl pyrrolidone, N-ethyl pyrrolidone, cinnamyl alcohol, phenethyl alcohol, p-methyl benzyl alcohol, propylene carbonate, butyl cellosolve, methyl carbitol, ethyl carbitol, propyl carbitol, butyl carbitol, diethyleneglycol, diethyl ether and dipropyleneglycol diethyl ether. Typically the concentration of those solvents can be in the range from 0.5% to 40%, preferably 1-35%, more preferably 5-30%, by weight calculated to the total composition.

Optionally, aqueous colouring composition can comprise further hair conditioning agents such as silicone oils either volatile or non-volatile, natural and synthetic oils. Among silicone oils those can be added to the colouring composition include dimethicone, dimethiconol, polydimethylsiloxane, DC fluid ranges from Dow Corning, natural oils such as olive oil, almond oil, avocado oil, weizenkeim oil, ricinus oil and the synthetic oils, such as mineral oil, isopropyl myristate, palmitate, stearate and isostearate, oleyl oleate, isocetyl stearate, hexyl laurate, dibutyl adipate, dioctyl adipate, myristyl myristate and oleyl erucate.

Additional non-ionic conditioning agents may be polyols such as glycerin, glycol and derivatives, polyethyleneglycoles known with trade names Carbowax PEG from Union Carbide and Polyox WSR range from Amerchol, polyglycerin and polyethyleneglycol mono or di fatty acid esters.

Compositions may further comprise at least one ubiquinone of the formula

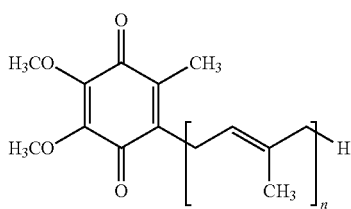

where n is a number between 1 and 10 at a concentration of 0.0001 to 1%, preferably from 0.0002 to 0.75%, more preferably from 0.0002 to 0.5% and most preferably from 0.0005 to 0.5% by weight, calculated to total composition.

The composition comprises ubiquinone which is preferably selected from the ones where n is a number between 6 and 10 and more preferably it is ubichinone 50 where n is 10, also known as Coenzyme Q10.

Composition can comprise at least one amino acid. At least one amino acid is comprised at a concentration of 0.01 to 10%, preferably 0.05 to 7.5% and more preferably 0.1 to 5% and most preferably 0.25 to 5% by weight calculated to total of each composition.

Aqueous coloring composition can comprise one or more amino acids. Suitable amino acids are glycin, histidine, citrullin, asparagine, alanin, valin, leucin, isoleucin, pyrolin, tryptophane, phenylalanine, methionine, serine, tyrosine, threonine and gluatamine. Preferably, the amino acid is selected from glycin, histidine, citrullin, asparagine, alanin, valin, leucin, isoleucin, pyrolin, serine, tyrosine, threonine and gluatamine. More preferably, at least one amino acid is selected from glycin, histidine, asparagine, alanin, valin, leucin, pyrolin, serine, tyrosine and gluatamine, and most preferably at least one amino acid is selected from glycin, asparagine, alanin, valin, leucin, and serine.

Aqueous colouring composition can comprise further ceramide type of compound at a concentration 0.01 to 3%, preferably 0.05 to 2.5% and more preferably 0.1 to 2% and most preferably 0.1 to 1.5% by weight calculated to total of each composition, with the general formula

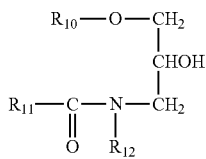

where $R_{10}$ and $R_{11}$ are independent from each other alkyl- or alkenyl group with 10 to 22 carbon atoms, $R_{12}$ is alkyl or hydroxyl alkyl with 1 to 4 carbon atoms group and n is a number between 1 to 6, preferably 2 or 3. Preferred compound according to the above chemical structure is cetyl-PG-hydroxyethylpalmitamide.

Further optional ingredient are sterols, especially the phytosterols as preferred hair restructuring agents, at a concentration 0.01 to 3%, preferably 0.05 to 2.5% and more preferably 0.1 to 2% and most preferably 0.1 to 1.5% by weight calculated to total of each composition. Especially preferred ones are of plant origin for example ergosterol, sitosterol, stigmasterol, fucosterol, brassicasterol, fungisterol, campesterol, zymosterol, ascosterol, cerevisterol, episterol, faecosterol, spinasterol. Among those phytosterols, the ones found in "Avocadin" which is the unsaponified fraction of the avocado oil is more preferred.

Aqueous coloring composition can comprise at least one diamine compound. Preferred diamide compounds are according to the general structure

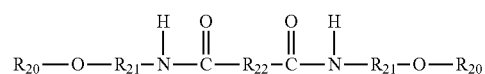

wherein $R_{20}$ is a linear or branched, saturated or unsaturated alkyl chain with 1 to 12 C atoms which may be substituted with hydroxy and/or alkoxy groups, preferably $R_{20}$ is linear or branched, saturated or unsaturated alkyl chain with 1 to 12 C atoms which may be substituted by 1 to 3 substituents selected from a hydroxy group and C1 to C6 alkoxy group, more preferably $R_{20}$ is a unsubstituted alkyl group with 1 to 12 C atoms, and alkyl group with 2 to 12 C atoms substituted by one or two hydroxyl groups, by one alkoxy group with 1 to 6 C atoms or by one hydroxyl and one alkoxy group with 2 to 6 C atoms, $R_{21}$ is linear or branched alkyl chain with 1 to 5 C atoms, preferably linear or branched alkyl chain with 2 to 5 C atoms and more preferably an alkyl chain with 2 to 3 C atoms, and $R_{22}$ linear or branched, saturated or unsaturated alkyl chain with 1 to 22 C atoms, preferably linear or branched, saturated or unsaturated alkyl chain with 11 to 22 C atoms.

Preferred individual diamide compounds are the ones according to the formula A to G.

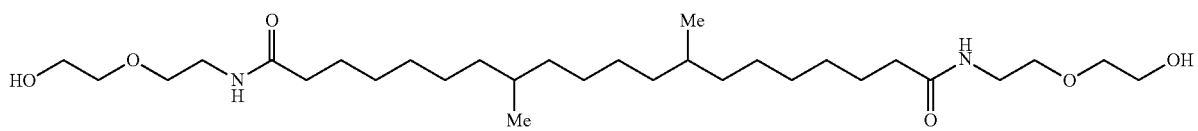

(A)

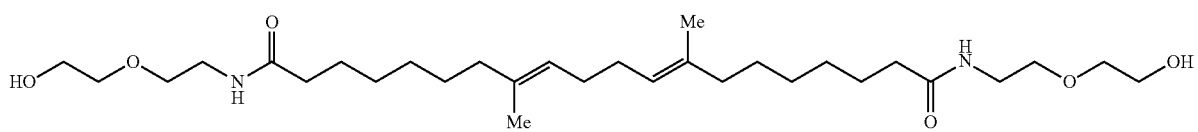

(B)

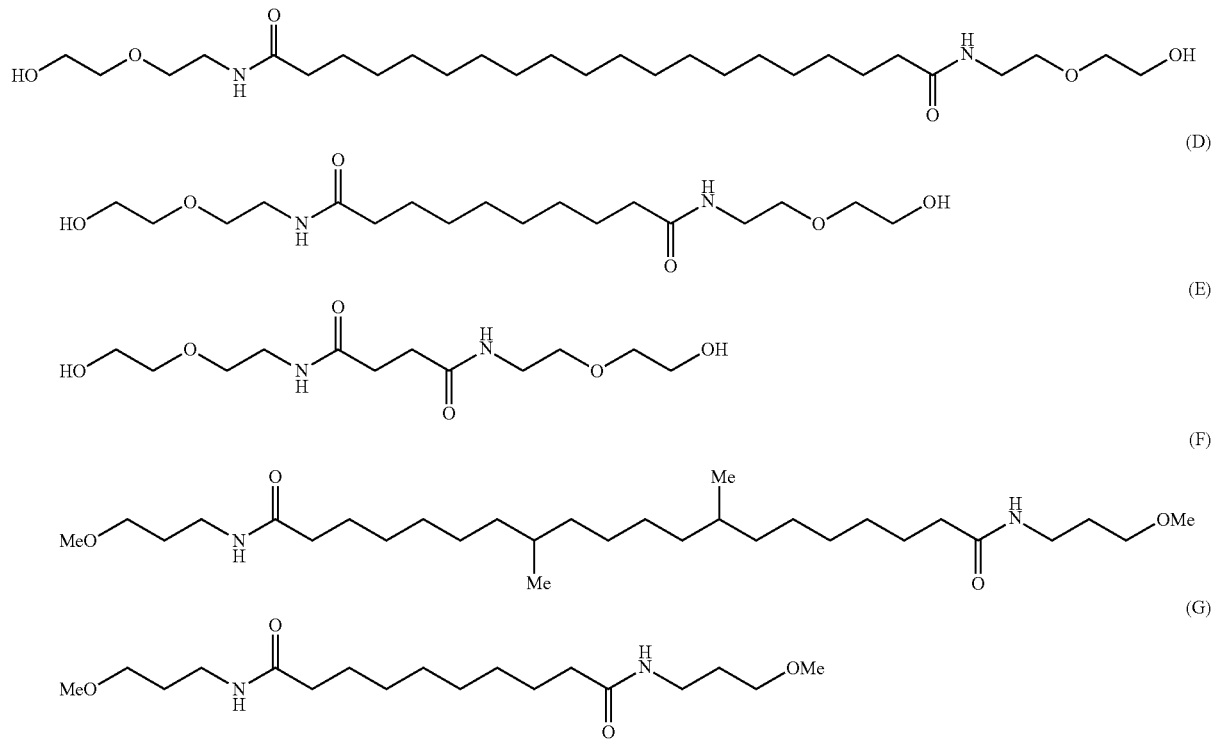

Particularly preferred diamide compound is the compound F which is bis(methoxypropylamido)isodocosane and commercially available from Kao Corporation—Japan.

Concentration of diamide compound is in the range of 0.001 to 5%, preferably 0.002 to 3% more preferably 0.005 to 2% and most preferably 0.01 to 1% by weight calculated to total composition.

Aqueous coloring composition can comprise additionally substances customarily found in colouring compositions such as preservatives, fragrance, sequestering agents.

The following example is to illustrate the present invention, but not to limit.

EXAMPLE 1

| Acid red 52 | 1 |
| Ethanol | 10 |
| Propylene carbonate | 20 |
| Dimethicone | 1 |
| Lactic acid | 4 |
| Xanthan gum | 1 |
| Fragrance | q.s |
| Water | to 100 |

Medium blond hair at a color level 6 of a consumer was colored with above composition. Prior to coloring hair consumer was shown the color to be achieved at the end of coloring and the expectation of the customer was met fully with a color direction red-blond.

EXAMPLE 2

The coloring composition of Example 1 was mixed with the following composition at various ratios.

| Acid orange 7 | 0.3 |
| Acid violet 43 | 0.8 |
| Ethanol | 10 |
| Propylene carbonate | 20 |
| Dimethicone | 1 |
| Lactic acid | 4 |
| Xanthan gum | 1 |
| Fragrance | q.s |
| Water | to 100 |

Mixed Coloring Compositions

|  | A | B | C | D | E |
| --- | --- | --- | --- | --- | --- |
| Example 1 | 10 | 25 | 50 | 35 | 75 |
| Example 2 | 90 | 75 | 50 | 65 | 25 |

The above compositions A, B, C and E were applied onto a sheet comprising 8 areas having each different natural hair color from level 3 (darkest) to 10 (lightest). The customer found the color to be achieved with the composition C too reddish and with the composition E too violet. On the basis of the finding, composition D was produced and shown on the sheet what the color approximately be at the end of the coloring process. The color direction was perfectly matched with the expectation of the customer and medium brown hair of the customer was colored to a red violet direction. It was noted that without the aid of the sheet, experimentation without actually coloring hair could not be performed and customer satisfaction could not be achieved.

The invention claimed is:
1. A hair coloring process with an aqueous composition having a dye component consisting of one or more direct dyes, comprising the steps of, in order:

applying at least two different aqueous compositions, each prepared to provide a different natural hair color, onto a sheet comprising two or more areas, each of said two or more areas receiving one of said different aqueous compositions, visualizing an expected color of hair at the end of the coloring process by reviewing the sheet, choosing one of said aqueous compositions, applying the chosen aqueous composition onto hair and processing thereon for 1 to 45 minutes, rinsing the chosen aqueous composition off from the hair, and optionally shampooing and/or drying the hair.

2. The process according to claim 1 wherein at least one of the at least two different aqueous coloring compositions comprises at least two direct dyes.

3. The process according to claim 1, wherein the sheet comprises two to fifteen areas, each area having a different natural hair color.

4. The process according to claim 3, wherein the two to fifteen areas are arranged as parallel strips on the sheet.

5. The process according to claim 1, wherein the sheet comprises cellulosic wood free paper weighing 140 g/m$^2$.

6. The process according to claim 1, wherein the aqueous coloring composition has a pH in the range of 1 to 10.

7. The process according to claim 1, wherein the aqueous coloring composition comprises at least one carboxylic acid selected from citric, malic, lactic and maleic acids.

8. The process according to claim 1, wherein the aqueous coloring composition comprises at least one gelling agent.

9. The process according to claim 1 wherein the aqueous coloring composition comprises at least one fatty alcohol and at least one emulsifying agent selected from anionic, nonionic, amphoteric (or zwiterionic) and/or cationic surfactants.

10. The process according to claim 9 wherein the least one emulsifying agent is selected from ethoxylated fatty alcohols and at least one cationic surfactant is selected from

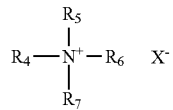

where $R_4$ is a saturated or unsaturated, branched or non-branched alkyl chain with 8-22 carbon atoms or

where $R_8$ is saturated or unsaturated, branched or non-branched alkyl chain with 7-21 carbon atoms and n has value of 1-4 or

where $R_9$ is saturated or unsaturated, branched or non-branched alkyl chain with 7-21 carbon atoms and n has value of 1-4, and $R_5$, $R_6$ and $R_7$ are substituted or unsubstituted, straight or branched, saturated or unsaturated lower alkyl chain with 1 to 4 carbon atoms, and X is chloride, bromide, methosulfate.

11. The process according to claim 1, wherein the one or more direct dyes are selected from anionic, cationic and neutral nitro dyes.

12. The process according to claim 11 wherein the one or more direct dyes are selected from anionic dyes.

13. The process according to claim 1, wherein the aqueous coloring composition comprises at least one organic solvent.

* * * * *